(12) United States Patent
Wu et al.

(10) Patent No.: US 10,406,021 B2
(45) Date of Patent: Sep. 10, 2019

(54) METHOD AND SYSTEM FOR PRODUCING AND DELIVERING AIRLESS MEDICAL ICE SLURRY TO INDUCE HYPOTHERMIA

(71) Applicants: Yue Wu, Memphis, TN (US); Yue Shao, Memphis, TN (US)

(72) Inventors: Yue Wu, Memphis, TN (US); Yue Shao, Memphis, TN (US)

( * ) Notice: Subject to any disclaimer, the term of this patent is extended or adjusted under 35 U.S.C. 154(b) by 805 days.

(21) Appl. No.: 14/908,227

(22) PCT Filed: Aug. 1, 2014

(86) PCT No.: PCT/IB2014/063606
§ 371 (c)(1),
(2) Date: Jan. 28, 2016

(87) PCT Pub. No.: WO2015/019257
PCT Pub. Date: Feb. 12, 2015

(65) Prior Publication Data
US 2016/0175141 A1    Jun. 23, 2016

Related U.S. Application Data

(60) Provisional application No. 61/862,131, filed on Aug. 5, 2013, provisional application No. 61/862,139, filed on Aug. 5, 2013.

(51) Int. Cl.
*A61F 7/00* (2006.01)
*A61F 7/12* (2006.01)
(Continued)

(52) U.S. Cl.
CPC .............. *A61F 7/0085* (2013.01); *A61F 7/12* (2013.01); *A61M 19/00* (2013.01);
(Continued)

(58) Field of Classification Search
CPC ........... F25C 1/20; F25C 1/125; A61F 7/0085
See application file for complete search history.

(56) References Cited

U.S. PATENT DOCUMENTS 7,389,653 B2 * 6/2008 Kasza ................... A61F 7/0085
62/342
8,505,315 B2 * 8/2013 Kasza ....................... F25C 1/00
606/44
(Continued)

*Primary Examiner* — Kaitlyn E Smith
(74) *Attorney, Agent, or Firm* — The Patent Practice of Szmanda & Shelnut LLC; James G. Shelnut

(57) ABSTRACT

The present invention relates to a method and system for producing and delivering sterile, airless, and highly loaded ice slurry for inducing therapeutic hypothermia. The method is capable of producing and delivering ice slurry in a patient to induce hypothermia through internal and external cooling methods such as subcutaneous, intravascular, intraperitoneal, gastrointestinal, and lung methods. The method is capable of producing and delivering saline ice slurry or other phase-change slurries compatible with human tissues. Ice slurry is made by crushing, smoothing, and mixing ice slush in an airtight and self-collapsible liquid container, followed by being pumped out through flexible tubing and injection port into a patient body without air. The novel method and system are simple, and easy to use, which facilitate long term storage, immediately ready to use, and airless delivery.

14 Claims, 7 Drawing Sheets

(51) Int. Cl.
*A61F 7/10* (2006.01)
*A61M 19/00* (2006.01)

(52) U.S. Cl.
CPC . *A61F 2007/0063* (2013.01); *A61F 2007/108* (2013.01); *A61F 2007/126* (2013.01)

(56) References Cited

U.S. PATENT DOCUMENTS

| | | | | |
|---|---|---|---|---|
| 2006/0161232 A1* | 7/2006 | Kasza | ................... | A61F 7/0085 607/105 |
| 2007/0056313 A1* | 3/2007 | Kasza | ................... | A61F 7/0085 62/353 |
| 2008/0236186 A1* | 10/2008 | Kasza | ................... | A61F 7/0085 62/342 |
| 2009/0255276 A1* | 10/2009 | Kasza | ...................... | F25C 1/00 62/68 |

* cited by examiner

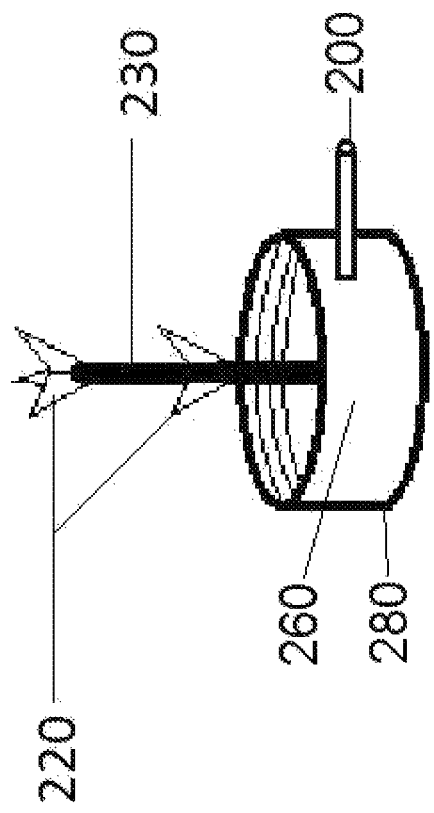
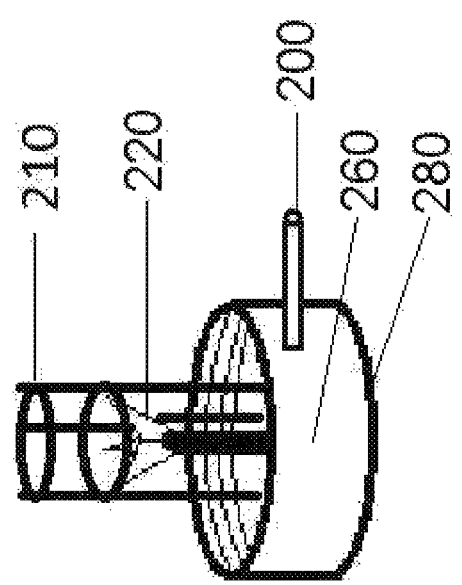
Fig. 4B
Fig. 4A

METHOD AND SYSTEM FOR PRODUCING AND DELIVERING AIRLESS MEDICAL ICE SLURRY TO INDUCE HYPOTHERMIA

PRIORITY

This application claims the benefit of U.S. Provisional Patent Application No. 61/862,131 filed Aug. 5, 2013 and U.S. Provisional Patent Application No. 61/862,139 filed Aug. 5, 2013, both of which are fully incorporated herein.

TECHNICAL FIELD

The present invention relates to a method for the preparation of sterile and airless medical ice slurry and using it for inducing hypothermia in a patient. Still more specifically this invention relates to an improved method and apparatus for the preparation, storage, and delivery of sterile medical ice slurry that is deliverable through a variety of small diameter catheters inserted into patient's blood vessel or body for inducing therapeutic hypothermia without introducing air bubbles into the blood stream.

BACKGROUND ART

Control of a patient's body temperature down to therapeutic hypothermia while undergoing medical treatments such as surgical procedures in the operating room, emergency room, or intensive care unit is beneficial. Despite various types of cooling apparatus and methods have been utilized in the past for inducing therapeutic hypothermia, it lacks a rapid and efficient cooling technology to meet the time window for optimal efficacy.

Recently, ice slurry was introduced to as a method to achieve hypothermia. It allows rapid and highly controlled cooling of a specific organ or group of organs and in most cases allows multiple targets or whole body to be protectively cooled to optimum individually protective temperatures.

The use of medical ice slurry to induce hypothermia is known in the art. A slurry of frozen saline is administered through injection means to rapidly cool organs to reduce metabolic demand and increase the likelihood of cell survival during periods of oxygen deprivation. A different number of apparatuses are utilized to create and produce the medical ice slurry utilized in this process.

For example, U.S. Pat. No. 6,547,811 by Lance B. Becker, Terry Vanden Hoek, and Kenneth E. Kasza issued Jul. 2, 2002, and entitled "Method for Inducing Hypothermia" discloses systems for phase-change particulate slurry cooling equipment and methods to induce hypothermia in a patient through internal and external cooling. Subcutaneous, intravascular, intraperitoneal, gastrointestinal, and lung methods of cooling are carried out using saline ice slurries or other phase-change slurries compatible with human tissue. Perfluorocarbon slurries or other slurry types compatible with human tissue are used for pulmonary cooling. Traditional external cooling methods are improved by utilizing phase-change slurry materials in cooling caps and torso blankets. U.S. Pat. No. 7,389,653 B2 by Kenneth E. Kasza et al., discloses an apparatus for producing sterile ice slurries for medical cooling applications. The apparatus includes a slurry production reservoir adapted to contain a volume of a saline solution, or other solution containing a freezing point depressant. A flexible membrane crystallization surface is provided within the slurry production reservoir. The membrane is chilled to a temperature below a freezing point of the saline solution within the reservoir such that ice particles form on the membrane. A deflector in the form of a reciprocating member is provided for periodically distorting the membrane and dislodging the ice particles, which form on the membrane.

U.S. Pat. No. 8,505,315 published Aug. 13, 2013, filed Feb. 6, 2009, by Kenneth E. Kasza et al., discloses an apparatus for producing sterile ice slurries for medical cooling applications. The ice slurry production apparatus includes a blender container receiving sterile saline carrier liquid and sterile chunk ice, a cutter blade, a slurry conditioning-agitator mechanical mechanism coupled to blender cover, a slurry delivery tube and a tubing pump, and an electric power transformer for controlling blender speed.

DISCLOSURE OF INVENTION

Technical Problem

Principal aspects of the present invention are to provide an enhanced method and device for the preparation, storage, and delivery of sterile medical ice slush and slurry. Important aspects of the present invention are to provide such method and device for the producing and delivering of sterile medical ice slurry substantially without negative effect and that overcome some of the disadvantages of prior art arrangements.

For instance, U.S. Pat. No. 8,505,315 teaches the use of a blender device. This patent teaches the creation of sterile slurry modules which are placing the saline solution and ice in the form of cubes or crushed ice, which are then emptied into a blender, which chops the ingredients of the slurry modules to create ice particles of the desired size. One of the main problems with this blender method of making ice slurry is that start-up of the motor under peak load conditions—i.e., with the blender filled with ice and saline solution—often require large power to operate blender motor. Additionally, the use of ice cubes or chopped ice causes the blender blades to make a great deal of heat while melting the ice particles and reducing the ice loading rapidly. Moreover, its mechanism is limited because the open use of the blender is likely to create an unnecessary and dangerous level of air in the medical slurry. As the blender chops up the chunks of ice and sends the medical slurry to a delivery tube, air surrounding the slurry can be incorporated to the medical slurry. The air incorporated into the medical slurry has the capability to form unwanted gas bubbles in the delivery system of the medical slurry. These gas bubbles may be delivered intravenously to the patient receiving the medical slurry. As such, these gas bubbles may cause the patient to experience an arterial gas embolism. Additionally, the blender device needs a conditioning-agitator mechanical mechanism to enhance mixing, further complicated the system. Therefore, what is needed is a simple method and device which may create and deliver sterile medical slurry efficiently without incorporating gas into the slurry.

ADVANTAGEOUS EFFECTS OF INVENTION

Advantageous Effects

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

In summary, the state of the art related to the preparation of fine sterile medical ice slurry comprises: methods and devices for efficient and rapid production and delivery of medical ice slurry through small diameter medical catheters without blending gas bubbles into.

In accordance with features of the invention, a method and a system utilize: an airtight deformable container containing sterile pre-conditioned ice slurry ingredients, an agitator used to crush, smooth, and mix the slurry ingredients into ice slurry, An outlet port coupled by a slurry delivery tube, a slurry delivery tubing pump, and an associated specially designed slurry injector tip connected to the discharge end of a pump tube is used to pump slurry out of the deformable container. A variable electric power transformer is used to control agitator speed and cycle during the crushing, smoothing and mixing, and delivering processes. The tubing pump through calibration allows the setting of slurry delivery rate and also tracts amount delivered both of which facilitate reaching a targeted protective cooling temperature.

In accordance with features of the invention, the use of the partially frozen slush with weak molecular bonding for the production of medical ice slurry rather than solid or chunk ice in prior art generates less heat to melt the ice in crushing process and require less power assumption. Therefore a light duty power supply and electric motor is sufficient, which is favor to miniaturize the system.

In accordance with features of the invention, a less rigid container can be used in the system rather than a rigid blender container. An airtight deformable container prevents air being blended in the ice slurry, which is essential for deliver ice slurry via blood stream. The container collapses while the ice slurry is pumped out. The collapsed container wall pushes ice slurry toward the mixing device and the outlet port, and reduces the need of an additional conditioning-agitator mechanical mechanism.

Moreover, the option of using pre-conditioned ice slush in an airtight deformable container eliminates transferring ingredients into additional blender container for pumping. The preparation, storage, and delivery of ice slurry can be processed in the same container without additional transfer process, which maintains the sterility. Blender ingredients preparation procedures provide improved capability for making medical sterile slurry from sterile slush and enable quick and reliable delivery of sterile slurry.

In accordance with features of the invention, the ice slush can be formed in the airtight deformable container, and be stored in the same container at right condition for long period of time such as a week, before being converted to ice slurry and being used in patient. The long term storage warrants a massive production in practice.

In accordance with features of the invention, the components which have direct contact with ice slush or slurry can be disposables, reducing the re-sterilization challenge.

Still other objects of the present invention will become readily apparent to those skilled in this art from the following description wherein there is shown and described the embodiments of this invention, simply by way of illustration of one of modes suited to carry out the invention. As it will be realized, the invention is capable of other different embodiments and its several details are capable of modifications in various obvious aspects all without departing from the scope of the invention. Accordingly, the drawing and descriptions will be regarded as illustrative in nature and not as restrictive.

BRIEF DESCRIPTION OF DRAWINGS

Description of Drawings

Figure 1:
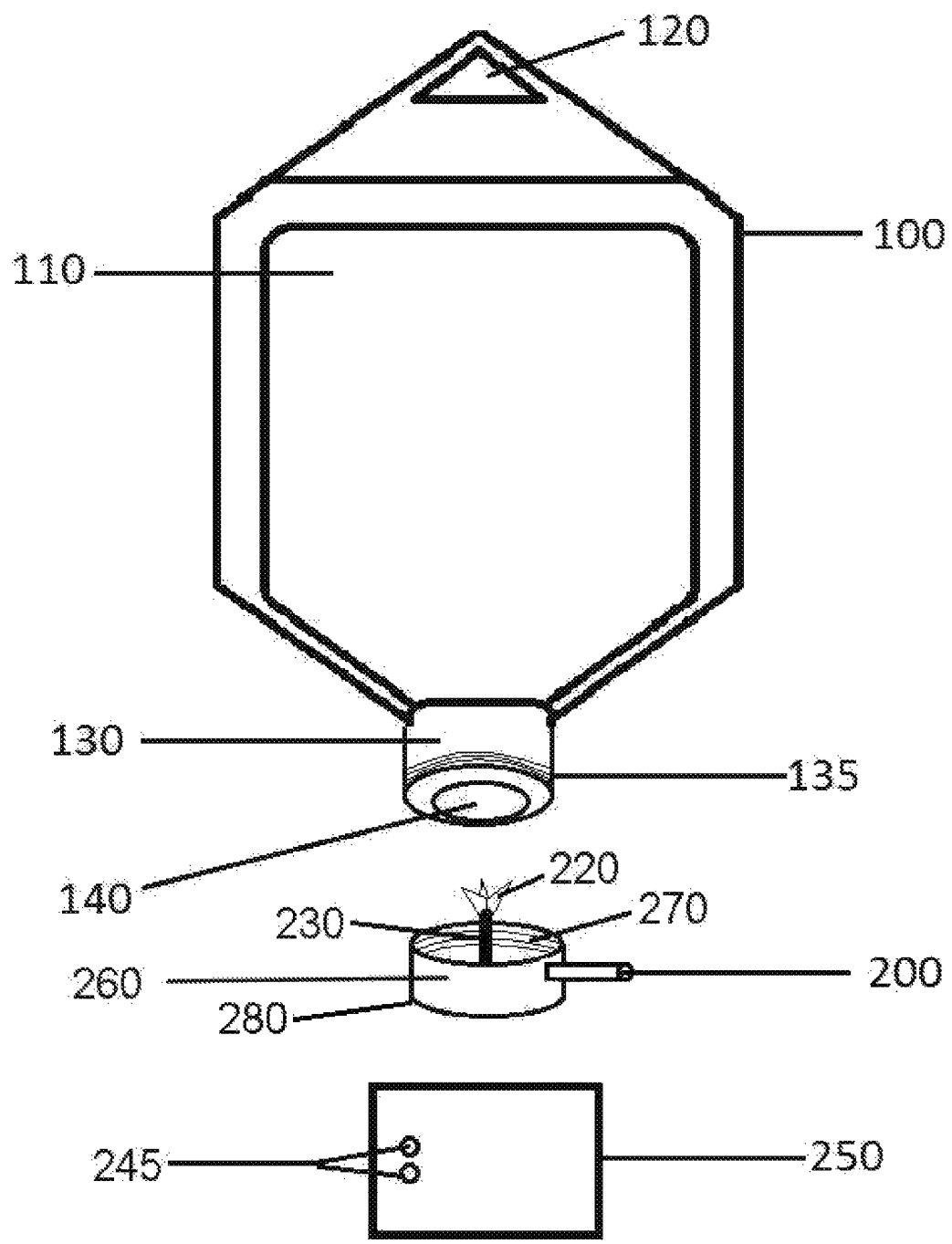

Various exemplary embodiments of this invention will be described in detail, wherein like reference numerals refer to identical or similar components, with reference to the following figures, wherein:

FIG. 1 is a side view of the self-collapsible container, mixing device, and driver.

Figure 2:
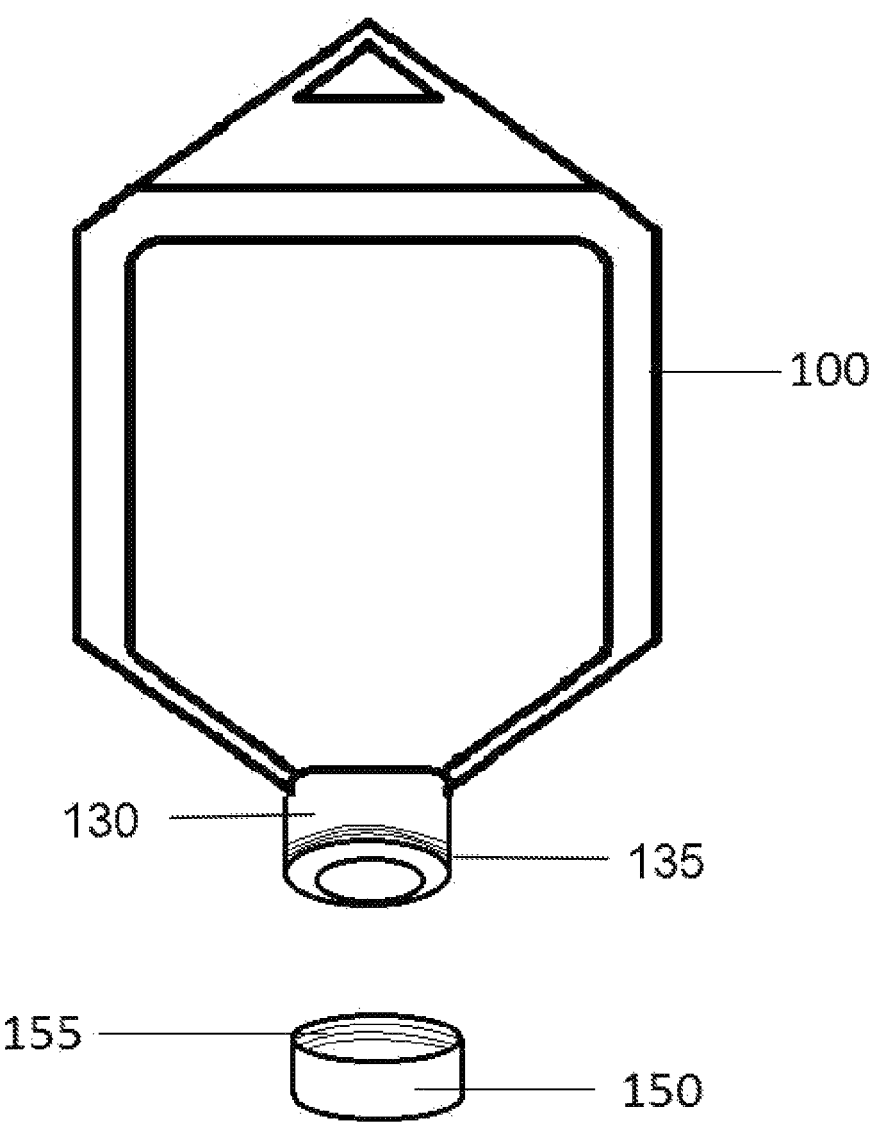

FIG. 2 is a side view of the self-collapsible container with a storage lid.

Figure 3:
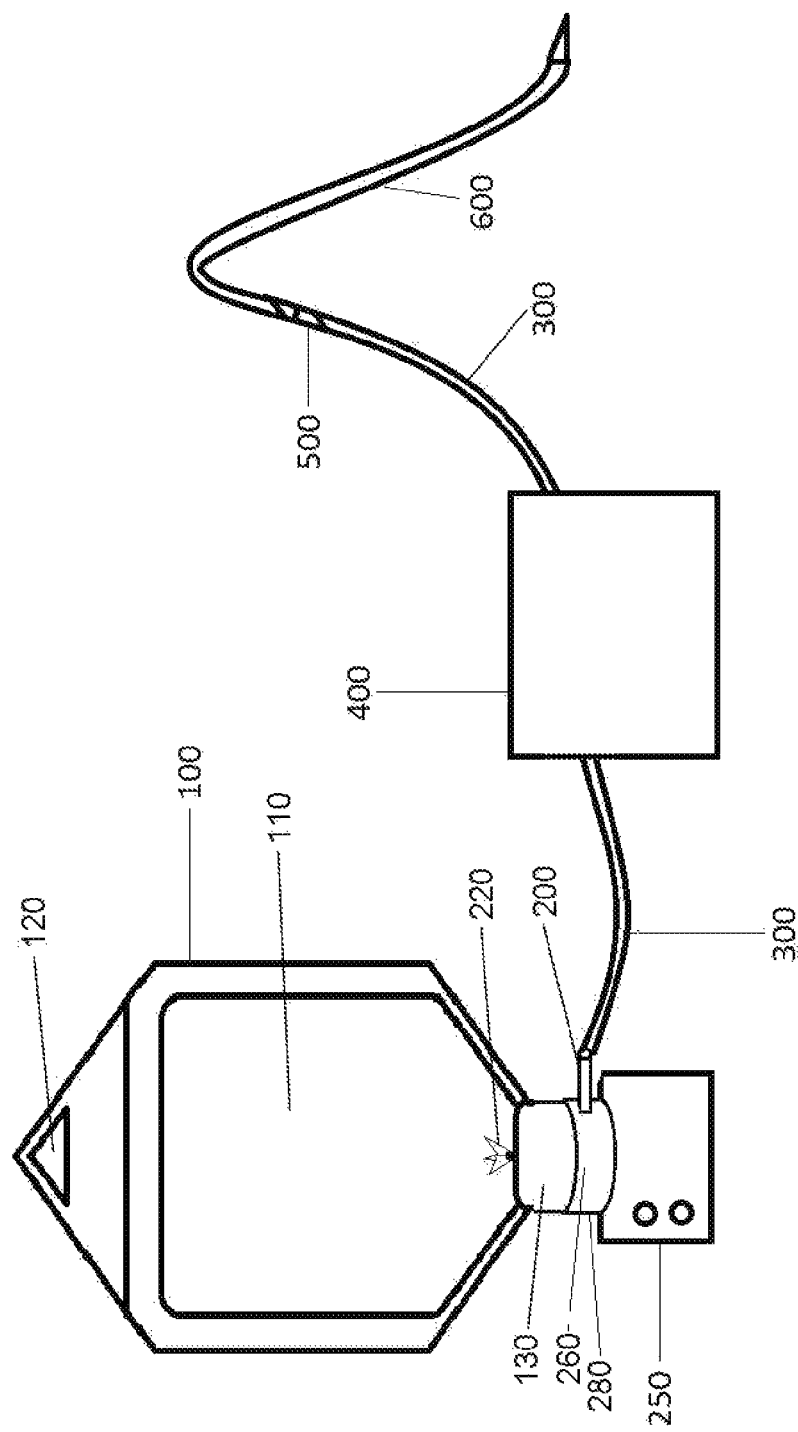

FIG. 3 is a side view of the self-collapsible container attached to the mixing device and the mixing device connected to a pump device.

FIG. 4A is a side view of another embodiment of the mixing device.

FIG. 4B is a side view of another embodiment of the mixing device.

Figure 5:
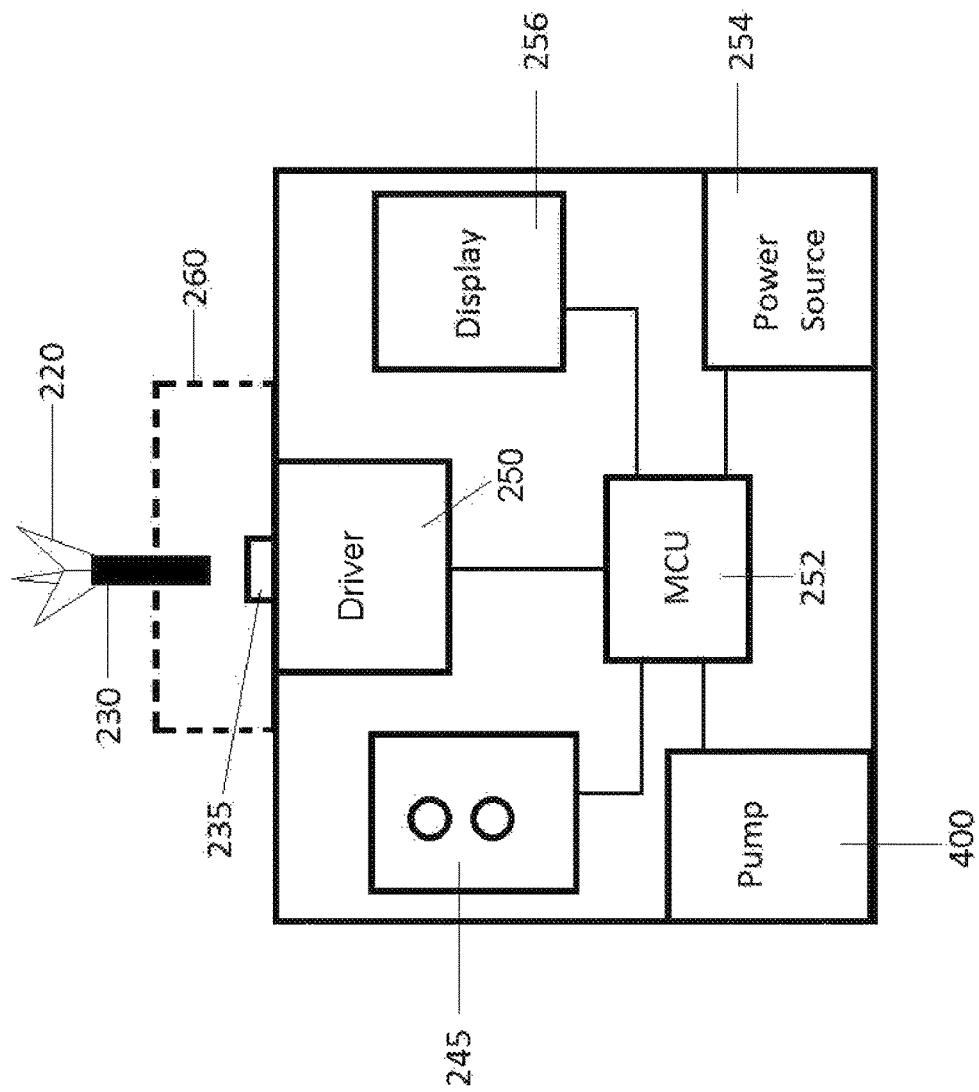

FIG. 5 is a schematic view of integrated producing and delivering system.

Figure 6:
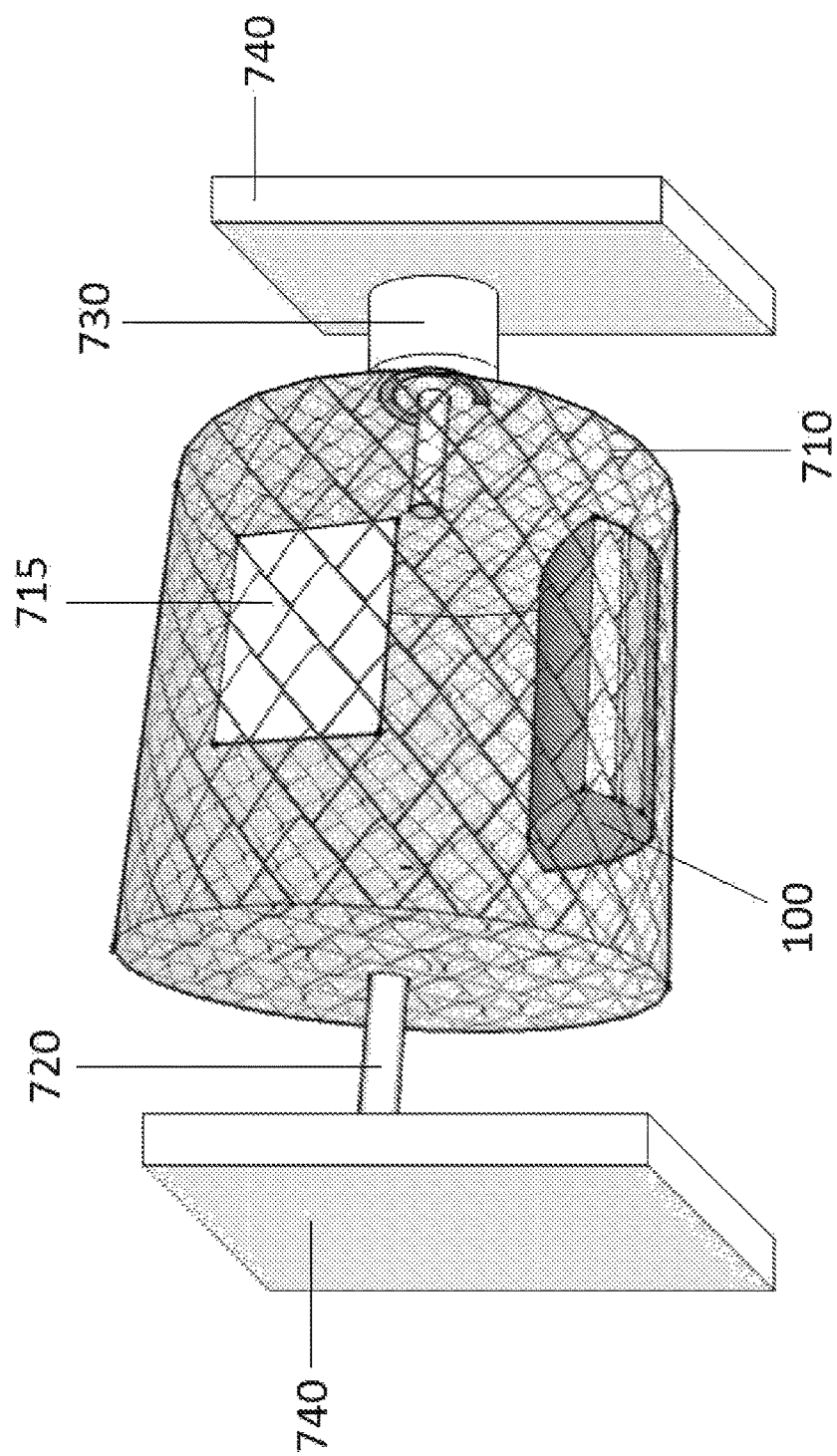

FIG. 6 is a perspective view of an embodiment of the slurry ingredients formation device.

Figure 7:
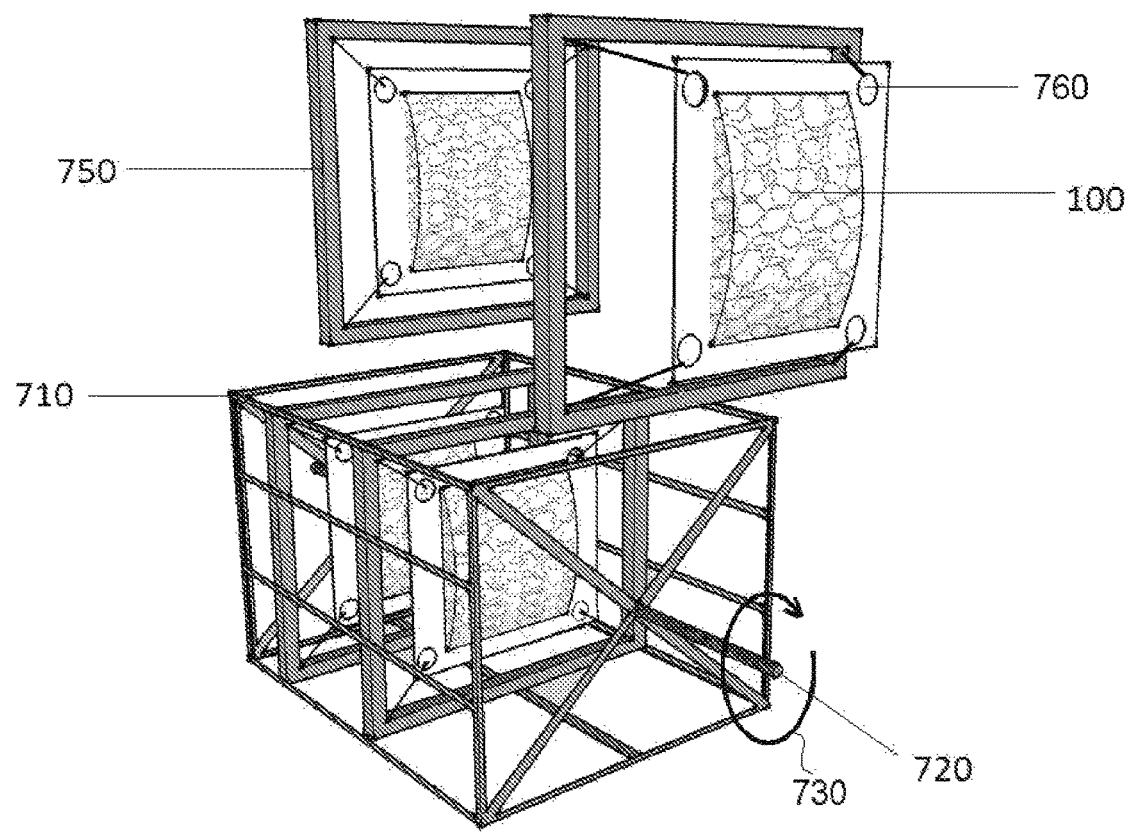

FIG. 7 is a perspective view of another embodiment of the slurry ingredients formation device.

BEST MODE FOR CARRYING OUT THE INVENTION

Best Mode

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

In literature, ice slush and ice slurry are both defined as a mixture of small ice crystals and liquid water. The ice slush and ice slurry are used interchangeably without commonly agreed distinction. In this application, the ice slush is different from ice slurry with the main advantage of the latter being able to pump through small sized tubing, e.g. a catheter which has 7-French (~2.33 mm) diameter. At present invention, 'slurry ingredients' is used to referring both, when they are added in invented device as ingredients and before being pumped out.

The medical ice slurry production and delivery is made by two general steps, each has multiple variations. Step 1: Fill an airtight and self-collapsible container, which has a mouth opening, with slurry ingredients. The self-collapsible container and its content of slurry ingredients may be stored at the storing temperature (such as −1.0° C.) for several days before being used. During the storage, a lid is used to seal the mouth opening. Step 2: Before being on a patient body, the lid for storage is removed. A mixing device, with an agitator and an outlet port, is attached to the airtight and self-collapsible container via the mouth opening. If air entered into the container during the attaching, the air will be removed by pointing the outlet port upwards and squeezing the air bubble out through the outlet port. The outlet port is connected to a flexible tubing. The other end of the flexible tubing connects to a medical port/catheter directly or via an adaptor for delivering the ice slurry into patient. The agitator mixes and agitates the slurry ingredients in the container to breaks the weak bonds between ice particles into fine and smooth particles during operation. Thus the slurry ingredients are converted into ice slurry which is pumpable through small sized tubing. Then the ice slurry is pumped out through the outlet port by a pump via the flexible tubing, and through the medical port/catheter into the patient without air bubble.

To make sterile ice slurry, the following components should be sterile: the slurry ingredients, and the inner surfaces of the container, flexible tubing, catheter, and the mixing device. If a peristaltic pump is used, the pump element need not be sterile.

The process of preparing the slurry ingredients for step 1 can be done through many number of methods. One of methods involves filling liquid solutions in an airtight and self-collapsible container, slowly rotating the container in a cooling unit, and stopping the freezing process after a set fraction of water (such as <70%) is frozen. The mouth opening of the container is covered by a removable lid after the container is filled. The liquid solutions are mixture of water, at least one type of freezing point depressing chemical(s), and zero or more other types of chemical(s) and/or component(s) (e.g. blood plasma). The rotation of the container provides top and bottom circulation so the mixture is well mixed with the same temperature. When the temperature of the mixture is below freezing temperature, the initial phase change (water freezing into micro ice nuclei) happens in the container homogenously. The circulation keeps the solution mixed and tends to promote an even temperature distribution. The freezing of ice continues into forming a soft dendritic form, whose bond between the ice particles is easy to break. After additional mixing and smoothing, there is no big particles or sharp edge inside the slush ingredients. During the operation the self-collapsible container may be partially filled under its maximum filling capacity. No air is allowed in the container through the collapse of the container wall. A mixing device may be used to replace the lid to seal the air tight container during freezing and storing to reduce operation procedure.

The partially filling of the container and the absence of air further promote the deforming of the flexible container wall when the liquid flows inside the flexible container during the rotation. The deforming of the container wall acts as an extra mixing feature to: 1) evenly mix the ice and liquid mixture across the container, 2) scrape off the thin dendritic ice layer frozen on the inner surface of the container wall, 3) prevent the forming of big ice crystals, and 3) break up larger crystal matrices and promote the creation and maintenance of a small slush mixture (as opposed to coarse).

Alternative method of preparing the slurry ingredients may use the method disclosed in U.S. Pat. No. 7,874,167 by filling the airtight and self-collapsible container with saline or other chemical solution and seal the mouth opening with a lid.

Another method is to transfer the ice slurry made by the method disclosed in U.S. Pat. No. 5,402,644 or the method disclosed in U.S. Pat. No. 8,505,315 into the airtight and self-collapsible container as slurry ingredients for airless delivery.

Referring to FIG. 1, one of the embodiments of the invention is displayed. The system utilizes a container 100 and a mixing device 280. The container 100 has a collapsible pouch 110 which holds the slurry ingredients. The container 100 has a hanging point 120 which allows a user to hang the container 100 from a supporting hook. One end of the container 100 has a container neck 130. The container neck 130 has a mouth opening 140. The container neck 130 has an external neck thread 135 which allows the container 100 to be attached and secured to the mixing device 280. The container neck 130 could be formed from a rigid material.

The mixing device 280 has a container attachment 260 for attaching the container 100 to the mixing device 280. The container attachment 260 has an internal attachment thread 270 which is complementary to the external neck thread 135. It may have a rubberized or silicone gasket or o-ring (not shown) to further ensure an airtight fit between the container 100 and container attachment 260. The outlet port 200 is located on the side wall of container attachment 260. The mixing device has an agitator 230. The agitator 230 has a long rotational axel which terminates in a plurality of agitating protrusions 220. The agitator 230 is driven by a driver 250, which is controlled by a control means 245. A user can operate the driver 250 via the control means 245. When the driver 250 is turned on the agitator 230 rotates about its longitudinal axis. The user can also control the speed at which the agitator 230 rotates via the control means 245. The agitator 230 rotates around the rotational axis, causing the agitating protrusions 220 to spin around. The agitator 230 serves multiple purposes: crushing and smoothing big ice particles into fine particles and mixing the ice and liquid mixture during the delivery with constant or variable speed. The control means 245 may be any type of structure or means which permits a user to turn on the driver 250 and control the speed of use. For instance the control means 245 could be one or more knobs, one or more switches, one or more buttons, a touchscreen, any combination of these elements, or merely an on/off in power supply. Those of skill in the art may find that the ice slurry may be used directly by removing it from container 100 through mouth opening 140.

Referring to FIG. 2, the container 100 may be stored prior to being attached to the mixing device 280. To ensure that the slurry ingredients do not leak from the container 100, a container lid 150 may be placed on the container neck 130. The container lid 150 is also placed on the container neck 130 during the formation process of forming the slurry ingredients. The container lid 150 may have a rubberized or silicone gasket or o-ring (not shown) to further ensure an airtight fit between the container 100 and container lid 150. In the embodiment shown the container lid 150 has a lid internal thread 155 which is complementary to the external neck thread 135.

The means of securing the container 100 to the mixing device 280 or container lid 150 may be made through any known means or other embodiments. The referenced figures display a means of securing by screwing the container 100 onto the mixing device 280 or container lid 150. The container 100 may be attached to the mixing device 280 or container lid 150 by snapping the components together or using another attachment means that creates an airtight seal between the container 100 and the mixing device 280 or the container lid 150.

Referring to FIG. 3, the conjunction between the container 100 and the mixing device 280 and the utilization of the system is displayed. The container 100 is attached by to the mixing device by securing the container neck 130 to the container attachment 260 on the mixing device 280. In the embodiment displayed the external neck thread 135 (shown in FIG. 1) is threaded to the internal attachment thread 270 (shown in FIG. 1) to removably secure the container 100 to the mixing device 280. The container neck 130 and container attachment 260 form an airtight connection to prevent any leakage of medical ice slurry from the container 100 and prevent the intrusion of any air into the container. A rubberized or silicone gasket or o-ring (not shown) may be placed within the container attachment 260 to further ensure an airtight fit between the container 100 and mixing device 280. When the container 100 is secured to the mixing device 280, the agitator 230 protrudes through the mouth opening 140 of the container and contacts the slurry ingredients in the container 100.

The container 100, containing slurry ingredients, is secured to the mixing device 280. Initially, the agitator 230 stirs to crush big ice particles and break the conglomeration of ice particles for short period of time, such as 20 seconds, then a pump 400 starts to pump the ice slurry out of the outlet port 200 and continues through a flexible tubing 300. The medical ice slurry is pumped out of the container 100 by the pump 400. The medical ice slurry is delivered to the patient through the flexible tubing 300 and an injection port 600. The flexible tubing 300 and the injection port 600 may be interfaced with an adapter 500.

The mixing device 280 is installed to the container 100 after removing the container lid 150 which is used during freezing and storing. The outlet port 200 is plugged into the flexible tubing 300. The flexible tubing 300 is routed through a pump 400, which is used to pump medical ice slurry through the injection port 600 for a particular medical cooling application. The pump 400 may be any pump known to those with skill in the art, such as a peristaltic pump. The injection port 600, such as various catheters or medical ports, known for different medical applications are connected to the other end of flexible tubing 300 directly or via a tubing adaptor 500. The slurry ingredients, the inside of the container 100, the mixing device 280, the flexible tubing 300, tubing adaptor 500, and the injection port 600 have direct contact with ice slurry have to be sterile for making a sterile ice slurry. A driver 250 will drive the agitator 230 (shown in FIG. 1) to crush, smooth, and mix slurry ingredients.

A wire guard 210 may be used to protect the cutting or scratching of the collapsible pouch 110 from the agitator 230 as referred by FIG. 4A. In this embodiment the mixing device 280 has a wire guard 210 which is placed around the agitator 230. The wire guard 210 prevents the agitating protrusions 220 from coming in contact with the collapsible pouch 110 in the container 100. If a wire guard 210 is not used, the container neck 130 and the lower portion of the container which connects to the neck 130 may be made of rigid material to protect the pouch being cut when it collapse due to air pressure.

Referring to FIG. 4B, other embodiments of the mixing device 280 could be used. In these embodiments the agitator 230 is elongated and contains multiple sets of agitating protrusions 220. The agitating protrusions 220 may be flat blades (as shown) or spherical balls (not shown) which cut, smooth, and agitate the slurry ingredients in the collapsible pouch 110. The agitator 230 may be in any length or shape sufficient to rotate about a longitudinal axis to stir the medical ice slurry. The agitator 230 may have any number of agitating protrusions 220 placed in any location on the agitator 230. The agitating protrusions 220 may be any shape sufficient to break the medical ice slurry and mix the slurry. Each blade may have different shape and design associated with different functions such as cutting, mixing and circulating. The agitator 230 and agitating protrusions 220 may be made of any material, including but not limited to metal or plastic, such as stainless steel or polyethylene or polystyrene. Protective means, such as a wire guard, may be used to prevent the pouch being cut by the protrusions.

FIG. 5 is a scheme of one embodiment with the driver 250 and the pump 400 being integrated. The mixing device 280 is connected to the driver 250, which gets power from a power source 254. The power source 254 may be an external power source or an internal power source. The driver 250 and the pump 400 are controlled by a microcontroller (MCU) 252, which may be any type of central processing unit. The MCU 252 receives commands from the control means 245 for the settings of driver 250 and pump 400. A user can control the producing and delivering of medical ice slurry through the control means 245. The MCU 252 may display information at a display screen 256. The display screen 256 displays information such as status of ice slurry, the amount of ice slurry pumped through the mixing device 280 and the pump rate setting.

The display screen 256 may also display rotation speed or setting of the driver 250. The MCU 252 controls the driver 250. The driver 250 provides the rotation to the agitator 230. In some embodiments the driver 250 may cause the agitator 230 to rotate both clockwise and counterclockwise. The driver 250 may also cause the agitator 230 to move in a longitudinal direction. In this manner the agitator 230 may move further into the container 100 and back out in and in and out motion. This motion may be made while the agitator 230 rotates. The agitator 230 is connected to the driver 250 by a motor shaft attachment 235. The agitator 230 may be permanently or removeably attached to the mixing device 280. In one embodiment, the agitator 230 may be removed and replaced with another agitator 230. The exterior of the mixing device 280 and the driver 250 may have features such as a pair of matching groove and bulge respectively to prevent the relative rotation between the two.

The utilization of the system will now be described. First a known amount of slurry ingredients are produced elsewhere and transferred to the flexible and self-collapsible container 100 via the mouth opening 140. In other option, ice slush can be directly made by putting the container 100, which is filled with saline solution and closed with a container lid 150, in a cooling unit. The container lid 150 is replaced by the mixing device 280 before pump and delivery. The mixing device 280, which has the same matching threads as container lid 150, is screwed onto mouth opening 140 to seal the container to prevent air entering and liquid leaking. If there is air in the container, it can be removed via the outlet port 200 by orienting the outlet port 200 upward and squeezing air out through outlet port 200. Once air is removed, a flexible tubing 300 is connected to the outlet port. The flexible tubing 300 may be clamped by any known means such as the roller of a peristaltic pump to prevent air getting into the container 100.

The mixing device 280 with an agitator 230, driven by a driver 250, is used to mix/agitate the liquid and ice mixture. The agitator 230 also breaks the weak bonds between ice particles to form fine particles during operation and smooth the sharp edges and rough surfaces of the ice particles. A selected mixing speed or energy level is selected together with a selected mixing duration to further cause ice particles suspending in the ice slurry mixture. The slurry fluidity depends on ice fraction, the size and shape of the ice particles, and the evenly mixing of the mixture. A flexible tubing 300, such as a silicone delivery tubing, connects the outlet port 200, the adaptor 500 (optional), and the injection port 600, which is inserted into the patient. The pump 400 transports the ice slurry through the above components from container 100 to patient while the agitator 230 is mixing and agitating the ice slurry mixture.

The container 100 is flexible and self-collapsible due to the collapsible pouch 110. While the ice slurry is pumped out, the collapsible pouch wall collapses (by air pressure) and pushes slurry particles and liquid toward the outlet port 200 and pushes the ice slurry into the vortex caused by the agitator 230. The airtight feature of the container 100 prevents air from getting into ice slurry from outside of the container 100, eliminating air embolism for intravascular applications, and forces the container 100 to collapse and push the ice slurry to the vortex. Preventing air from entering the container 100 also forces the space between ice particles to be occupied by liquid, facilitating the flowing of the mixture.

One of ordinary skill in the art will recognize that other choices and arrangements of components could be made in order to deliver ice slurry without air embolism. The following are examples only and are not intended to limit the scope of the invention. The agitator 230 may be tilted at various angles from the axis of the container 100 to ensure thorough mixing of the ice particles and liquid, and preventing the creation of undesirable stagnant pools of unmixed slurry within the container 100. The axis of the container 100 may be in directions other than up and down. The outlet port 200 can be integrated on the container 100 instead of being incorporated on the container attachment 260.

One of ordinary skill in the art will recognize that the mixing device 280 can be at places other than bottom of the container, such as located at the top of the container 100. The top or bottom location is referring to the direction of gravity force. In this embodiment the mixing device 280 may be mounted on a wall or on a medical cart with the container attachment 260 positioned downwards. The container 100 is then attached onto the container attachment 260 from below. The ice slurry is pumped out from the outlet port 200 at top. Since ice particles in ice slurry have a lower density than water, the ice particles flow to the top of the slurry mixture. Pumping from the top may increases the ice fraction of delivered ice slurry while a squeezing device may be required to push the contents of the container upwards.

A squeezing device may be applied on the wall of container 100. The squeezing device could be a pair of rollers, a pair of squeezing pads or inflatable cuff connected to an air pump. The squeezing device may provide additional agitation and mixing effect on the collapsible pouch 110 to the ice slurry. The squeezing device could be coupled to move towards or opposite to each other to squeeze and mix the ice slurry.

One of ordinary skill in the art will recognize that the mixing device 280 may also be at side of the container 100. The location is referring to the direction of gravity force.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The slurry ingredients are formed in the container 100 prior to connecting the container 100 to the mixing device 280. The slurry ingredients may be formed in any manner and any known process. Referring to FIG. 6, a novel slurry ingredients formation device is displayed. The formation device has a rotating member 710 for holding the container 100 (the container neck is omitted for simplification of the figures). The rotating member 710 may hold one or more containers 100 during the formation process. In the embodiment displayed the rotating member 710 is a cylindrical wire frame. The rotating member 710 has an opening 715 to permit a user to add and remove containers 100. The rotating member 710 is attached at either end of the cylinder to an axel 720. One axel 720 is connected to a motor 730 which provides rotational power and movement to the rotating member 710. On one side the axel 720 is connected to a support frame 740. On the opposite side the motor 730 is connected to another support frame 740.

The container 100 is placed directly in the rotating member 710 via an opening 715. The opening 715 is opened for receiving or removing the container 100, and remains close during the slurry ingredients formation and storage. When the rotating member 710 rotates, the container 100 rotates/tumbles freely in the rotating member 710. Those of skill in the art will appreciate that the rotating member 710 may be a wired frame or mesh, or a container with plenty of wholes.

To form pre-conditioned slurry ingredients, the novel device is placed within a cooling unit (not shown). The cooling unit has a door (not shown) to open to receive or remove rotating member 710 and to shut to maintain the air temperature to cool the container 100. The container 100 is filled with mixture of water, at least one type of freezing point depressing chemical(s) such as sodium chloride, and zero or more other types of chemical(s) and/or component(s) (e.g. blood plasma or blood substitute). The rotating member 710 rotates while the containers 100 are cooled to turn the enclosed fluid solution into ice liquid mixture. The rotating member 710 rotates relative to its axle 720, which is mainly horizontal, installed through holes on the sidewall of cooling unit. A motor 730 placed outside or inside the cooling unit is used to rotate the rotating member 710 by providing rotation energy to the axle 720. Those of skill in the art will appreciate that for cooling unit (not shown), a range of cooling systems could be used including but not limited to a standard compressor type system or a solid state Peltier cooling system.

The purpose of the cooling unit (not shown) is to chill the air surrounding the container 100 below the freezing point of the mixture within the container 100. The cooling unit may be adapted to include one or more device(s) such as fans (not shown) to circulate the cooled air to promote the cooling speed of the container 100, and the even distribution of air temperature in cooling unit.

The rotation of the container 100 provides top and bottom circulation so the mixture is well mixed and has no temperature gradient. When the temperature of the mixture is below freezing temperature, and the initial phase change (water freezing into micro ice nuclei) happens in the container 100 homogenously. The circulation keeps the solution mixed and tends to promote an even temperature distribution. Thus the ice nuclei distributes randomly across the whole body. The freezing of ice continues into soft dendritic form, which is easy to break, without big particles or sharp edges.

During operation, if a flexible and deformable container 100 is used, the container 100 can be partially filled under its maximum capacity. The intended partially filling capacity and the absence of air promotes the deforming of the collapsible pouch 110 when liquid flows inside the collapsible pouch 110 during the rotation. The deforming of the collapsible pouch 110 acts as an external mixing mechanism so the mixture is evenly mixed. This deforming also provides a periodical distorting to scrape off the thin dendritic ice layer frozen on the inner surface of the wall of the collapsible pouch 110 and breaks up larger crystal matrices to promote the creation and maintenance of a fine slush mixture.

The deforming of the collapsible pouch 110 acts as an external mixing device to: 1) evenly mix the mixture across the container 100, 2) scrape off the thin dendritic ice layer frozen on the inner surface of the collapsible pouch 110, 3) prevent the forming of big ice crystals, and 4) break up larger crystal matrices and promote the creation and maintenance of a fine slush mixture (as opposed to coarse).

The container 100 may have exterior bagging to protect the sterility of the inner container's exterior surface during the operation. It is not necessary to maintain sterility for the cooling unit and rotating member 710.

The cooling unit regulates its internal air temperature to within a specified range to allow slush/slurry of ice and liquid mixture to be produced and maintained. A temperature control system of the cooling unit can have an initial target temperature that is well below the freezing point to expedite the initial freezing of slush/slurry but then have a separate maintenance temperature intended for storage when the mixture reaches a set ice fraction. This maintenance temperature is set at or above the temperature of the mixture. The air temperature in cooling unit is allowed to fluctuate above and below the target temperature (as with a normal two temperature control scheme that results in a saw tooth temperature profile).

Referring to FIG. 7, another embodiment of the slurry ingredients formation device is displayed. In this embodiment the rotating member 710 is adapted to accept support frame(s) 750. In this embodiment an axel 720 is connected at each end of the rotating member 710. One axel 720 is connected to a motor 730 which provides rotational power and movement to the rotating member 710. In this embodiment the motor 730 may be within the cooling unit (not shown) or placed outside of the cooling unit (not shown).

The rotating member 710 is designed to hold one or more support frame(s) 750 that a container 100 is fastened onto. The support frame 750 can receive one container, or may be adapted to receive more containers.

Each container 100 is attached to the support frame 750 by one or more attachment points 760. Each support frame 750 is then secured to the rotating member 710. The support frame 750 can be secured to the rotating member 710 by any means. In the displayed embodiment each support frame 750 slides into one of a number of slots located in the rotating member 710 which hold the support frames 750. The container 100 is fastened on a support frame 750 via fastening techniques known to those with skill in the art, such as via a clamp, clip or Velcro. The container 100 attaches to the support frame 750 via attachment points 760 on the edges of the container 100. One with ordinary skill in the art will recognize that other choices and arrangements of components could be made in order to fasten the container 100 to the support frame 750. The following are examples of alternatives. The support frame may 750 receive more than one container. The container 100 may have exterior bagging to protect the inner container's outer surface sterility, thus the attachment points 760 are on the external bagging. The attachment points 760 could be located on the container's peripheral edges/corners or on the body of external bagging. Attachment points 760 which are located on the peripheral edges or corners are attached to support frame 750 via attachment mechanisms known to those of skill in the art, such as a clamp, clip or Velcro. The support frame 750, along with the container 100, is fastened on the rotating member 710 via mechanism known to those of skill in the art.

The suspension of the containers 100 in the rotating member 710 prevents the shock and big deformation of the container 100 at low temperature. This feature facilitates a long term storage to prevent the leakage of the container 100 from the fatigue the material.

The rest of the device structure and operating steps are similar for both embodiments such as the temperature control, the container, and its contents. During the freezing and storing the ice slush, the motor 730 drives the rotating member 710 to rotate about the rotating axle 720, and causes support frame 750 to rotate. This in-turn causes the container 100 to rotate. The container 100 may be rotated at a relatively slow speed (~60 rpm). However, a broad range of speeds may be used. The rotation speed is determined by the balance between evenly mixing/agitating the mixture and the fatigue of the collapsible pouch 110 due to continuously deforming in long period of storage.

One of ordinary skill in the art will recognize that other choices and arrangement of components could be made in order to effect the rotation of the containers 100. The following are examples only and are not intended to limit the scope of the invention. The motor 730 could be located inside of the cooling unit (not shown). The motor 730 may drive the rotating member 710 directly or via roller chains, belt, or gear(s). The support frame 750 may be arranged other than parallel. The support frame 750 may be arranged so that it orbits around the rotating axle 720, instead of spinning around. The rotating member 710 and support frame 750 could be coupled together as one piece to receive the container 100.

One with skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A system for producing and delivering ice slurry, comprising:
   a. a deformable container comprising a mouth opening through which material can pass into an internal cavity of the deformable container and containing slurry ingredients for use;

b. a mixing device comprising an agitator, the device removably attached to the deformable container, the agitator positioned inside the interior of the deformable container, to form an air-tight closed container;

c. a driver for driving the agitator;

d. an outlet protruding from the deformable container or from the mixing device for material passing in or out of the deformable container;

e. a delivery tubing whose first end is connected to the outlet port;

f. a pump to move ice slurry out from the deformable container through the outlet port and the delivery tubing;

wherein the deformable container and the removably attached mixing device form an enclosed space in which the ice slurry is created.

2. The system for producing and delivering ice slurry of claim 1 wherein the slurry ingredients comprises chemical constituents of water, one or more types of freezing point depressing chemical, and zero or more types of other chemicals and components.

3. The system for producing and delivering ice slurry of claim 1 wherein the deformable container comprises a flexible, semi-flexible, partially rigid or partially flexible wall.

4. The system for producing and delivering ice slurry of claim 1 wherein the pump is a peristaltic pump.

5. The system for producing and delivering ice slurry of claim 1 wherein the agitator comprises a plurality of agitating protrusions rotating around the rotational axis which inclines relative to vertical direction in any angle.

6. The system for producing and delivering ice slurry of claim 1, further comprising a wire guard surrounding the agitator.

7. The system for producing and delivering ice slurry of claim 1, further comprising an injection port configured to connect to the delivery tubing.

8. The system for producing and delivering ice slurry of claim 1, further comprising means for applying mechanical force to the deformable container to facilitate further smoothing and moving of the ice slurry.

9. The system for producing and delivering of ice slurry of claim 1, further comprising an external mechanical device wherein the external mechanical device comprises one or more pair of rollers, a pair of squeezing pads, an inflatable cuff connected to an air pump, or an ultrasonic device.

10. A method for producing and delivering airless ice slurry, comprising:

a. providing a deformable container comprising a mouth opening through which materials can enter into the internal cavity of the deformable container;

b. preparing the deformable container containing slurry ingredients for use;

c. providing a mixing device which comprises an agitator;

d. providing a pump and a delivery tubing;

e. securing the deformable container to the mixing device so the agitator can pass through the mouth opening into the deformable container to contact the slurry ingredient and form an airtight seal;

f. causing the agitator to agitate, smooth, and mix the slurry ingredient to the ice slurry; and g. pumping the ice slurry out of the deformable container via an outlet port through the delivery tubing to facility the delivery of the ice slurry.

11. The method for producing and delivering airless ice slurry of claim 10 wherein the slurry ingredients comprises chemical constituents of water, one or more types of freezing point depressing chemical, and zero or more types of other chemicals and components.

12. The method for producing and delivering airless ice slurry of claim 10 wherein the means for preparing the deformable container containing the slurry ingredients comprises:

a. filling a mixture of a predetermined amount of water, one or more types of freezing point depressing chemical, and zero or more types of other chemicals and components into the deformable container through the mouth opening or the outlet port;

b. sealing the deformable container to restrain the mixture inside the deformable container;

c. placing the deformable container in a cooling unit;

d. rotating and tumbling the deformable container inside the cooling unit during cooling;

e. whereby the mixture freezes into the slurry ingredients.

13. The method for producing and delivering airless ice slurry of claim 10, further comprising a cooling unit and means for:

i. receiving the deformable container which contains a mixture of predetermined amount of water, one or more types of freezing point depressing chemical, and zero or more types of other chemicals and components;

ii. controlling the internal air temperature of the cooling unit to fluctuate around a predetermined freezing temperature to freeze the mixture to the slurry ingredient; and iii. controlling the internal air temperature of the cooling unit to fluctuate around a predetermined storing temperature for storing the slurry ingredients.

14. A method for preparing, producing, and delivering ice slurry, comprising:

a. Obtaining a device comprising:
  i. a deformable container comprising a mouth opening through which material can pass into the internal cavity of-the deformable container; and
  ii. a cooling unit;
  iii. a mixing device comprising an agitator;
  iv. a driver;
  v. an outlet protruding from the deformable container or from the mixing device for materials passing in or out of the deformable container;
  vi. a delivery tubing; and
  vii. a pump;

b. filling the deformable container with a predetermined amount of a mixture of water, at least one type of freezing point depressing chemical, and an optional chemical component;

c. sealing the deformable container to restrain the mixture inside the deformable container and placing the sealed deformable container into the cooling unit;

d. rotating and tumbling the deformable container in the cooling unit;

e. monitoring the temperature of the cooling unit using a temperature sensor;

f. controlling the temperature of the cooling unit to fluctuate around a predetermined freezing temperature in order to cool the mixture into a slurry ingredient; and g. controlling the temperature of the cooling unit to fluctuate around a predetermined storing temperature for storing the slurry ingredient until ready for use;

h. removing the deformable container containing the slurry ingredients from the cooling unit;

i. securing the deformable container to the mixing device to form an airtight seal, the agitator is positioned to pass through the mouth opening into the deformable container to contact the slurry ingredient;
j. connecting the outlet port to the first end of the delivery tubing;
k. causing the driver to move the agitator to fracture, smooth, and mix the slurry ingredients to generate an ice slurry at constant or variable speed; and
l. pumping the ice slurry out from the deformable container through the outlet port and the delivery tubing;
wherein the deformable container collapses during the step of pumping the ice slurry out from the deformable container.

* * * * *